(12) United States Patent
Feldser et al.

(10) Patent No.: US 9,567,642 B2
(45) Date of Patent: Feb. 14, 2017

(54) METHODS AND PRODUCTS RELATED TO TARGETED CANCER THERAPY

(71) Applicant: Massachusetts Institute of Technology, Cambridge, MA (US)

(72) Inventors: David Feldser, Somerville, MA (US); Tyler E. Jacks, Newtown, MA (US); Leah Marie Schmidt, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/376,482

(22) PCT Filed: Feb. 1, 2013

(86) PCT No.: PCT/US2013/024391
§ 371 (c)(1),
(2) Date: Aug. 4, 2014

(87) PCT Pub. No.: WO2013/116686

PCT Pub. Date: Aug. 8, 2013

(65) Prior Publication Data
US 2015/0218645 A1    Aug. 6, 2015

Related U.S. Application Data

(60) Provisional application No. 61/594,002, filed on Feb. 2, 2012.

(51) Int. Cl.
| A61K 39/395 | (2006.01) |
| C12Q 1/68 | (2006.01) |
| G01N 33/574 | (2006.01) |
| A61K 45/06 | (2006.01) |
| C07K 16/28 | (2006.01) |

(52) U.S. Cl.
CPC ....... *C12Q 1/6886* (2013.01); *A61K 39/39558* (2013.01); *A61K 45/06* (2013.01); *C07K 16/2827* (2013.01); *G01N 33/57484* (2013.01); *C12Q 2600/106* (2013.01); *G01N 2800/52* (2013.01)

(58) Field of Classification Search
CPC ............ A61K 39/395; A61K 39/39533; A61K 39/3955; A61K 39/39558; A61K 47/42; A61K 47/48; A61K 47/48384; A61K 47/48561
See application file for complete search history.

(56) References Cited

U.S. PATENT DOCUMENTS

| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 5,053,394 A | 10/1991 | Ellestad et al. |
| 5,208,535 A | 5/1993 | Nakayama et al. |
| 5,770,710 A | 6/1998 | McGahren et al. |
| 5,877,296 A | 3/1999 | Hamann et al. |
| 2002/0006413 A1 | 1/2002 | Sobol et al. |
| 2007/0065436 A1 | 3/2007 | Hariharan et al. |
| 2009/0162404 A1 | 6/2009 | Podack |
| 2010/0189716 A1 | 7/2010 | Molina et al. |
| 2010/0203010 A1 | 8/2010 | Hariharan et al. |

FOREIGN PATENT DOCUMENTS

| WO | WO 94/11026 A2 | 5/1994 |
| WO | WO 96/40260 A2 | 12/1996 |
| WO | WO 2008/121821 A1 | 10/2008 |

OTHER PUBLICATIONS

Li, Y., et al., J. Immunol., 153(1): 421-428, 1994.*
Bhat, S., et al., Expert Opin. Biol. Ther., 10(3): 451-458, 2010.*
Yeh, K.-Y., et al., Cellular Immunology, 165: 217-224, 1995.*
Chari et al., Immunoconjugates containing novel maytansinoids: promising anticancer drugs. Cancer Res. Jan. 1, 1992;52(1):127-131.
Erbe et al., Small molecule ligands define a binding site on the immune regulatory protein B7.1. J Biol Chem. Mar. 1, 2002;277(9):7363-8. Epub Dec. 6, 2001.
Feldser et al., Stage-specific sensitivity to p53 restoration during lung cancer progression. Nature. Nov. 25, 2010;468(7323):572-5. doi: 10.1038/nature09535.
Uvebrant et al., Discovery of selective small-molecule CD80 inhibitors. J Biomol Screen. Jun. 2007; 12(4):464-72. Epub Apr. 13, 2007.
Vitetta et al., Redesigning nature's poisons to create anti-tumor reagents. Science. Nov. 20, 1987;238(4830):1098-104.
Jilani et al., A clinical guide to tumour markers categorized under cancer types—A review. Baltic Journal of Comparative and Clinical Systems Biology. 2012;1:3-25.
Martinez-Paniagua et al., The pivotal role of yin yang 1 (YY1) inhibition (and downstream Bcl-2/Bcl$_{xl}$) by Galiximab (anti-CD80 mAb) in the reversal of resistance of B-NHL cells to chemotherapy. Blood (ASH Annual Meeting Abstracts) 2010;116: Abstract 2887.
Mir et al., Signaling through CD80: an approach for treating lymphomas. Expert Opin Ther Targets. Aug. 2008;12(8):969-79. doi: 10.1517/14728222.12.8.969.
Ren et al., Gene therapy for human nasopharyngeal carcinoma by adenovirus-mediated transfer of human p53, GM-CSF, and B7-1 genes in a mouse xenograft tumor model. Cancer Biother Radiopharm. Oct. 2008;23(5):591-602. doi: 10.1089/cbr.2007.0447.

* cited by examiner

*Primary Examiner* — Misook Yu
*Assistant Examiner* — Anne Holleran
(74) *Attorney, Agent, or Firm* — Wolf, Greenfield & Sacks, P.C.

(57) ABSTRACT

The invention relates to methods and related products for treatment and determining modes of treatment for cancer or prognosis of cancer. Preferably the methods are related to the induction of CD80 in p53 responsive cancer cells.

9 Claims, 14 Drawing Sheets

Inducible p53 function in mouse lung adenocarcinoma cell line transplants

KPrLG $Kras^{G12D}$ $p53^{LSL/LSL}$ $Cre^{ER}$
Luciferase IRES GFP

Regression and NK cell activation in transplanted tumors after p53 restoration

NK cell lineages are required for tumor regression after p53 restoration

Tumor regression is more robust in NCR Nu/Nu than NSG recipients

*Identifying the molecular determinants of the p53 tumor immune surveillance network*
Research Plan

CD80 mRNA is induced upon p53 restoration

RT-PCR analysis identifies CD80 as a putative NK cell activating ligand

FIG. 8A unstained
FIG. 8B Cd86(B7.2)
FIG. 8C Cd80(B7.1)
FIG. 8D Restored 48 hours CD80 (but not functionally related CD86) is expressed on the cell surface after p53 restoration CD80 cell surface expression increases with time (MHC expression may not change)

CD80

MHC

Cell Culture

CD80 cell surface expression increases over time after p53 restoration

Orthotopic transfer

CD80 is not tamoxifen dependent

CD80 is induced by p53 restoration in cancer cells (LKR) but not in primary MEFs or by cytostatic effects of mir34a in cancer cells (7b)

Q-RT-PCR

Mouse Cd80 has a consensus p53 binding site

KPr10 Cells

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic Polypeptide

<400> SEQUENCE: 1
tcgtctttca caagtgtctt cag                                           23

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
ttgccagtag attcggtctt c                                             21
```

METHODS AND PRODUCTS RELATED TO TARGETED CANCER THERAPY

RELATED APPLICATIONS

This application is a national stage filing under U.S.C. §371 of PCT International application PCT/US2013/024391, filed Feb. 1, 2013, which claims priority under 35 U.S.C. §119(e) to U.S. Provisional Application Ser. No. 61/594,002, filed Feb. 2, 2012 entitled "METHODS AND PRODUCTS RELATED TO TARGETED CANCER THERAPY" the entire contents of which is incorporated herein by reference.

BACKGROUND OF INVENTION p53 is a tumor suppressor gene which plays a critical role in cell cycle regulation, and is involved in apoptosis, genomic stability, and inhibition of angiogenesis. For instance, p53 is known to be involved in DNA repair and maintaining growth arrest and ultimately inducing apoptosis if the cell is damaged. In humans, p53 is encoded by the TP53 gene. In some cases the TP53 gene becomes mutated upon exposure to chemicals, radiation, or viruses. These mutations are significant because over 50 percent of human tumors are associated with a mutation or deletion of the TP53 gene.

Lung cancer, in particular, is the leading cause of cancer death worldwide, non-small-cell lung cancer (NSCLC) representing 85% of lung cancer cases. Lung adenocarcinoma, a histologic class of NSCLC, is associated with recurrent mutations in several well-defined oncogenes and tumor suppressor genes. For instance inactivating mutations in the tumor suppressor gene p53 are found in 50% of cases.

SUMMARY OF INVENTION

In some aspects the invention is a method for characterizing a cell by determining whether CD80 is expressed in a cell from a subject, wherein if CD80 is expressed in the cell, the cell has activated p53. The CD80 expression may be examined in a cell in vivo, ex vivo or in vitro.

In some embodiments the cell is a cancer cell. Expression of CD80 in the cancer cell may be indicative of sensitivity by the cell to chemotherapeutic treatment. In some embodiments expression of CD80 is examined in a cell from a subject that has not yet been treated with a chemotherapeutic agent. In other embodiments the expression of CD80 is examined in a cell from a subject that has previously been treated with a chemotherapeutic agent.

The method optionally includes the step of detecting the presence of p53 in the cell. In some embodiments the p53 is a p53 mutant. In other embodiments the p53 is a normal p53. In yet other embodiments an increase in p53 expression levels or an increase in p53 activity is indicative of an efficacious cancer therapy.

In other embodiments the expression of CD80 in the cell is indicative of DNA damage in the cell.

The method is a method for monitoring the efficacy of a cancer therapy in a subject in some embodiments. The presence of CD80 expression on the cell indicates that the cancer therapy is efficacious.

The method is a method for assessing the prognosis for a subject having a cancer in other embodiments. The presence of CD80 expression on the cell indicates an improved prognosis relative to a subject having a cancer cell that lacks CD80 expression.

In some embodiments when the expression level of CD80 is higher than the level of a control sample, the subject is administered a chemotherapeutic agent.

In other aspects the invention is a method involving administering to a subject having a non-hematologic CD80 positive cancer an anti-CD80 binding molecule conjugated to a toxic compound in an effective amount to bind to and kill a CD80 positive cancer cell. In some embodiments the non-hematologic CD80 positive cancer is a lung cancer.

In yet other aspects the invention is a method involving determining the status of p53 in a cancer cell of a subject and administering to the subject an anti-CD80 binding molecule when the cancer cell has normal p53 or is capable of supporting p53 activity.

A method of treating a subject having cancer is provided according to other aspects of the invention. The method involves administering to a subject having cancer an anti-CD80 binding molecule and a p53 inducing agent in an effective amount to treat the subject having cancer.

In some embodiments the method further comprises the step of determining whether subject has a CD80 positive cancer.

In other embodiments the methods involve the step of determining whether subject has a CD80 positive cancer.

The methods may involve the further step of detecting the presence of p53 in the cancer cell. In some embodiments the p53 is a p53 mutant. In other embodiments the p53 is a normal p53. The p53 alternatively may be a p53 mutant that is capable of supporting p53 activity when treated with a p53 inducing agent.

The methods may involve the further step of administering to the subject a chemotherapeutic agent or a p53 inducing agent. The p53 inducing agent may be a p53 expression inducing agent or it may be a p53 activity inducing agent.

The anti-CD80 binding molecule may be, for instance, a peptide, an antibody, or a small molecule. Optionally the anti-CD80 binding molecule is conjugated to a toxic compound.

A kit is provided in other aspects of the invention. The kit includes one or more containers housing a reagent for detecting p53 functionality, a reagent for detecting CD80 expression, and instructions measuring p53 functionality and CD80 expression in a cancer cell.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A is a graph depicting the amount of B220+ NK cells/mg lung tissue for either control or restored KrasLA2; p53LSL/LSL. FIG. 2B is a photograph of mice treated as in FIG. 2A, before, at the time and following treatment.

DETAILED DESCRIPTION

Figure 1:
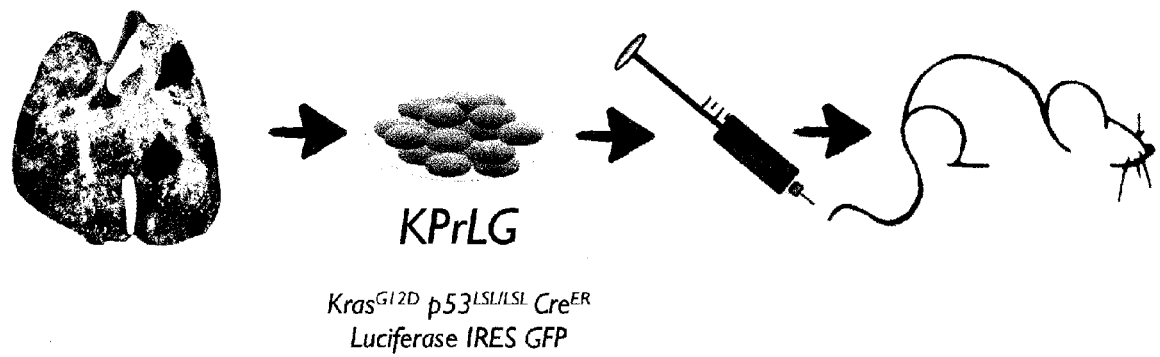
FIG. 1 is a schematic depicting inducible p53 function in mouse lung adenocarcinoma cell line transplants.

Methods for treating and determining effective therapies for patients having cancer are described herein. p53 plays an important role in tumor development. For example, the in vivo consequences of genetic restoration of p53 activity in established lung tumors has revealed that high grade tumor cells are cleared from established cancers in a mouse model of human lung adenocarcinoma.

It has previously been shown that increasing the amount of p53 through the restoration of endogenous p53 function can be useful in the treatment of cancer. Loss of p53 creates genomic instability that most often results in the aneuploidy phenotype. The p53 protein is known to control the cell cycle, which regulates cell division. In particular, the protein stops a cell from dividing when its DNA is damaged. It then activates DNA repair systems, and if the damage proves irreparable, it instructs the cell to undergo apoptosis. It is believed that sustained inactivation of p53 and other tumor suppressors is necessary for cancers to develop into late stages.

It has been discovered that natural killer (NK) cells of the innate immune system are an important component in this process of advanced tumor cell loss. It has also been discovered herein that the interaction between p53 and NK cells that results in tumor cell destruction is likely mediated by the up-regulation of the NK cell activating, cell-surface molecule CD80. Induction of CD80 mRNA in human and mouse lung cancer cells by multiple p53 activating stimuli has been observed. Additionally, cell surface expression of CD80 upon p53 activation in multiple mouse lung cancer cell-lines has been observed.

Cell surface expression of CD80 in response to p53 action is of significant clinical relevance. Initially CD80 is a biomarker of p53 action. The efficacy of anti-cancer therapies such as chemotherapeutics has been linked to the presence of normal p53 in cancer cells. The induction of CD80 upon p53 action renders CD80 a useful biomarker of anti-cancer therapy success. Further, CD80 expression in cells may be used as an indicator of DNA or other stress responses which could be useful for monitoring exposure to DNA damage agents or other cellular stresses, as an early indicator of potential diseased cells.

The findings of the invention are also useful in new therapeutic methods for the treatment of cancer. Specifically, knowledge that CD80 is expressed on the surface of p53 cancer cells provides the opportunity to deliver targeted toxic therapies directly to the cancer cells. The cell surface localization of CD80 allows CD80 binding molecule-mediated, such as antibody-mediated, therapies to specifically target p53 positive cancer cells. Binding molecules that facilitate cell destruction, either directly or indirectly by activating components of the immune system, could be utilized to augment or induce tumor regression.

The invention in some aspects involves the use of CD80 targeted therapies for the treatment of cancer and in particular embodiments, cancer with functional p53 or with activation or enhancement of p53. It has been discovered that p53 activity, e.g. wild type p53 or induction or activation of p53 results in CD80 cell surface expression. CD80 cell surface expression on cancer cells can be used in a variety of diagnostic, prognostic and therapeutic methods.

In one aspect, the invention is useful to screen a population of subjects to identify those that should be treated with an anti-cancer compound. The invention is also useful for identifying subjects that should be treated with a drug or therapy regimen that induces or activates p53 prior to or in conjunction with other anti-cancer therapies. These subjects are examined for the presence of a cancer having mutated p53. Additionally the methods are useful for identifying patients that are sensitive to therapy with a CD80 binding agent.

In one aspect, the invention is useful for identifying cancers that are responsive to anti-cancer treatment such as chemotherapy. In some embodiments, the presence of CD80 on the cell surface is assayed to determine the responsiveness of the cancer to therapy. For example, if CD80 is present on the cell surface the cell has activated p53 and is responsive to therapy. Any method known in the art for identifying the presence of CD80 can be used in the methods. Examples of relevant assays are described in more detail below. One simple and accurate method of analyzing the presence or absence of CD80 on the cell surface involves the use of flow cytometry.

The cell surface expression level can be compared to one or more control, reference or threshold levels to determine the responsiveness of the cancer to the therapy. One example of a control tissue for comparison is a normal tissue found in the local area. Known threshold levels for normal cells may also be used for comparison. The actual numbers in the particular determination of threshold values may vary for different tumors or under different circumstances, such as the conditions of the assay to determine expression. However, the skilled artisan would be able to identify the correct threshold values based on the circumstances. For example threshold values could easily be generated using normal non-cancerous tissue under similar circumstances. In each instance, the comparison of the expression levels of markers to a reference value is useful in determining the relative levels of marker in the test tumor cells.

The reference sample can be any of a variety of biological samples against which a diagnostic assessment may be made. Examples of reference samples include biological samples from control populations or control samples. Reference samples may be generated through manufacture to be supplied for testing in parallel with the test samples, e.g., reference sample may be supplied in diagnostic kits. Appropriate reference samples will be apparent to the skilled artisan.

The methods of the invention are useful for instance for determining whether a cancer is responsive or unresponsive to treatment with a therapeutic. A cancer that is "unresponsive to treatment by anti-cancer agents", is identified as one that does not express cell surface CD80. Thus, a subject having such a cancer will not be responsive to treatment with anti-cancer agents. The lack of cell surface expression indicates a lack of normal p53 activity. This may be due to loss of expression or activity due to mutations or other factors.

Whether a cancer is responsive or non-responsive to therapy can be further determined by determining the status of p53, i.e. Identifying the presence or absence of wild type p53 or p53 mutations.

As used herein, a tissue sample is tissue obtained from a tissue biopsy, a surgically resected tumor, or any other tumor cell mass removed from the body using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from a biopsy include gross apportioning of a mass, microdissection, laser-based microdissection, or other art-known cell-separation methods.

Because of the variability of the cell types in diseased-tissue biopsy material, and the variability in sensitivity of the predictive methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules or proteins. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids or proteins.

The presence and/or levels of CD80 and/or p53 may be measured using any of a number of techniques available to the person of ordinary skill in the art for protein or nucleic acid, e.g., direct physical measurements (e.g., mass spectrometry), binding assays (e.g., immunoassays, agglutination assays, and immunochromatographic assays), Polymerase Chain Reaction (PCR) technology, branched oligonucleotide technology, Northern blot technology, oligonucleotide hybridization technology, and in situ hybridization technology. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

The methods may involve the steps of isolating nucleic acids from the sample and/or an amplification step. Typically, a nucleic acid comprising a sequence of interest can be obtained from a biological sample, more particularly from a sample comprising DNA (e.g. gDNA or cDNA) or RNA (e.g. mRNA). Release, concentration and isolation of the nucleic acids from the sample can be done by any method known in the art. Various commercial kits are available such as the High pure PCR Template Preparation Kit (Roche Diagnostics, Basel, Switzerland) or the DNA purification kits (PureGene, Gentra, Minneapolis, US). Other, well-known procedures for the isolation of DNA or RNA from a biological sample are also available (Sambrook et al., Cold Spring Harbor Laboratory Press 1989, Cold Spring Harbor, N.Y., USA; Ausubel et al., Current Protocols in Molecular Biology 2003, John Wiley & Sons).

When the quantity of the nucleic acid is low or insufficient for the assessment, the nucleic acid of interest may be amplified. Such amplification procedures can be accomplished by those methods known in the art, including, for example, the polymerase chain reaction (PCR), ligase chain reaction (LCR), nucleic acid sequence-based amplification (NASBA), strand displacement amplification, rolling circle amplification, T7-polymerase amplification, and reverse transcription polymerase reaction (RT-PCR).

Polymerase chain reaction (PCR) technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA.

PCR primers can be designed routinely by those having ordinary skill in the art using sequence information. The mRNA or cDNA is combined with the primers, free nucleotides and enzyme following standard PCR protocols. The mixture undergoes a series of temperature changes. If the test gene transcript or cDNA generated therefrom is present, that is, if both primers hybridize to sequences on the same molecule, the molecule comprising the primers and the intervening complementary sequences will be exponentially amplified. The amplified DNA can be easily detected by a variety of well-known means. If no gene transcript or cDNA generated therefrom is present, no PCR product will be exponentially amplified.

PCR product may be detected by several well-known means. One method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable to perform a PCR reaction on the first PCR reaction product. The second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

Hybridization methods for nucleic acids are well known to those of ordinary skill in the art (see, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York). The nucleic acid molecules hybridize under stringent conditions to nucleic acid markers expressed in cancer cells. The nucleic acid markers disclosed herein are known genes and fragments thereof. Targets are nucleic acids selected from the group, including but not limited to: DNA, genomic DNA, cDNA, RNA, mRNA and may be natural or synthetic.

Binding assays for measuring CD80 may use solid phase or homogenous formats. Suitable assay methods include sandwich or competitive binding assays. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Detection of a protein in a test sample involves routine methods. The skilled artisan can detect the presence or absence of a protein using well known methods. One such method is an immunoassay. In general, immunoassays involve the binding of proteins in a sample to a solid phase support such as a plastic surface. Detectable antibodies are then added which selectively bind to the protein of interest. Detection of the antibody indicates the presence of the protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in Immunoassays for the 80's, A. Voller et al., Eds., University Park, 1981, which is incorporated herein by reference.

Simple immunoassays such as a dot blot and a Western blot involve the use of a solid phase support which is contacted with a test sample. Any proteins present in the test sample bind the solid phase support and can be detected by a specific, detectable antibody preparation. The intensity of the signal can be measured to obtain a quantitative readout. Other more complex immunoassays include forward assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, in a forward sandwich assay a third detectable antibody, which binds the second antibody is added to the system. Other types of immunometric assays include simultaneous and reverse assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional assays. A reverse assay involves the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody.

In some embodiments, the invention provides methods for treating a cancer patient including the step of administering to the patient a therapeutically effective amount of an anti-CD80 binding molecule. An anti-CD80 binding molecule, as used herein, refers to a compound that binds to CD80 on the surface of a cancer cell.

These molecules include but are not limited to small molecule and peptide based binding molecules. According to the invention useful CD80 binding molecules that are small molecules include any small molecule that binds to CD80 and preferably specifically binds to CD80. Specifically binds to CD80, as used herein, refers to only minimal non-specific binding, such that the small molecule does not cause intolerable side effects. This can be assessed using for instance national regulatory standards that are well known to the skilled artisan. In some embodiments specifically binds to CD80 indicates that the molecule does not cross-react with other CD proteins. CD-80 binding small molecules include but are not limited to those compounds described in Erbe D V et al J Biol Chem 2002; 277:7363-7368 and Uvebrant, et al Journal of Biomolecular Screening 12(4); 2007, as well as analogs and variants thereof and/or stereoisomeric forms, or pharmaceutically acceptable acid or base addition salt forms thereof, in therapeutically effective amounts. The disclosures of these publications are incorporated by reference herein in their entirety and particularly for the teachings related to chemical structures included therein.

In some embodiments the CD80 binding molecule is a CD80 binding peptide. The CD80 binding peptides of the invention bind to CD80, preferably in a selective manner. As used herein, the terms "selective binding" and "specific binding" are used interchangeably with respect to peptides to refer to the ability of the peptide to bind with greater affinity to CD80 and fragments thereof than to non-CD80 compounds. That is, peptides that bind selectively to CD80 will not bind to non-CD80 compounds to the same extent and with the same affinity as they bind to CD80 and fragments thereof. In some embodiments, the peptides of the invention bind solely to CD80 and fragments thereof. As used herein, a binding peptide that binds selectively or specifically to CD80 will bind with lesser affinity (if at all) to non-CD80 compounds. Lesser affinity may include at least 10% less, 20% less, 30% less, 40% less, 50% less, 60% less, 70% less, 80% less, 90% less, or 95% less.

The binding peptides useful according to the invention are isolated and include but are not limited to isolated peptides, isolated antibodies and isolated antibody fragments. "Isolated peptides" as used herein refer to peptides that are substantially physically separated from other cellular material (e.g., separated from cells which produce the antibodies) or from other material that hinders their use either in the diagnostic or therapeutic methods of the invention.

The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

CD80 antibodies are available commercially, from companies such as Abcam, AbD Serotec, Abnova, Thermo Scientific Pierce Antibodies, Advanced Targeting Systems, Novus Bio, BD Pharmingen and many others. The commercial antibodies may be used as is or modified or humanized by methods well known to the skilled artisan.

The CD80 binding molecules may be conjugated to a toxic material directly or indirectly, for instance, through a carrier such as microparticle which can deliver a payload. As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

Thus, some therapeutics of the invention are CD80 antibodies or other CD80 binding molecules conjugated to a cytotoxic or toxic agents. The conjugates include an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

For selective destruction of the cell, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the binding molecule and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

These binding molecules described herein can be administered as a single dose or in several doses administered over a period of time (e.g. chronic administration at regular intervals of time) as described herein.

In another aspect, the invention provides a combination therapy that includes a CD80 binding molecule and a p53 inducing agent. A p53 inducing agent is useful for treating a cancer that does not have normal p53, also referred to herein as a p53 negative cancer. A p53 negative cancer is one that has at least some cancer cells that do not have normal p53 activity. These cells may have some p53 activity and it may just be reduced compared to normal p53 activity levels. Alternatively these cells may have no p53 activity due, for instance, to a p53 mutation. Thus, in some embodiments, the invention provides methods for treating a cancer patient including the step of administering to the patient a therapeutically effective amount of a CD80 binding molecule and a therapeutically effective amount of a p53 inducing agent or a therapeutic preparation of these compounds. The CD80 binding molecule can be administered along with, before, or after the p53 inducing agent. In some embodiments, the CD80 binding molecule and p53 inducing agent can be formulated into a single therapeutic preparation.

A "p53 inducing agent" as used herein refers to an agent that restores p53 function to a cell. In some instances the cell may lack normal p53 function. p53 inducing agents include but are not limited to nutlins and drugs that reactivate mutant forms of p53. Nutlins are cis-imidazoline analogs which inhibit the interaction between mdm2 and p53, thus allowing p53 to be active in the cell. There are at least three nutlins referred to as Nutlin-1, Nutlin-2 and Nutlin-3.

In one aspect, the invention provides methods for the treatment of cancer. Cancer, as used herein, refers to an uncontrolled growth of cells which interferes with the normal functioning of the bodily organs and systems. Cancers, including those cancers which migrate from their original location and seed vital organs, can eventually lead to the death of the subject through the functional deterioration of the affected organs. Cancers can be classified into a variety of categories including, carcinomas, sarcomas and hematopoietic cancers. Carcinomas are malignant cancers that arise from epithelial cells and include adenocarcinoma and squamous cell carcinoma.

Cancers include but are not limited to biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some embodiments, the cancer is selected from the group consisting of lung cancer, bone cancer, brain and CNS cancer, connective tissue cancer, esophageal cancer, eye cancer, Hodgkin's lymphoma, larynx cancer, oral cavity cancer, skin cancer, and testicular cancer. In other embodiments the cancer is not a hematologic cancer. Hematologic cancers are cancers of the blood, bone marrow, and lymph nodes and include leukemia, lymphoma, and myeloma.

In some embodiments the cancer of the invention is a cancer characterized by cells having p53 activity. A cancer "characterized by cells having p53 activity", is a cancer comprising cancer cells that have normal p53 activity or induced p53 activity. Cells having p53 activity can be identified, for example, by assaying the levels and/or activation status of p53 or confirming that p53 is not mutated. Assays that can detect the level or activation status of proteins are known in the art and include western blots and protein array analysis.

The amount of CD80 or p53 in a cancerous tissue is preferably measured in a sample from a patient to be treated. In some embodiments, the amount is measured in vivo in a subject using one or more methods described herein or known in the art. In other embodiments, the amount is measured in a sample obtained from a subject suspected of having cancer or a patient diagnosed as having cancer. The sample can be a solid tissue biopsy or a biological fluid sample. The sample can contain essentially cancer cells. Alternatively, the sample can contain a mixture of cancer cells and non-cancer cells. The amount or presence of CD80 or p53 can be obtained directly or extrapolated using appropriate controls and/or standards.

As used herein, a subject is a human, non-human primate, cow, horse, pig, sheep, goat, dog, cat, or rodent. In all embodiments human subjects are preferred. In aspects of the invention pertaining to predictive therapy in cancers, the subject is a human either suspected of having the cancer, or having been diagnosed with cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography. Diagnostic methods for cancer and the clinical delineation of cancer diagnoses are well known to those of skill in the medical arts.

The therapeutic compounds described herein can be administered in combination with other therapeutic agents and such administration may be simultaneous or sequential. When the other therapeutic agents are administered simultaneously they can be administered in the same or separate formulations, but are administered at the same time. The administration of the other therapeutic agent, including chemotherapeutics can also be temporally separated, meaning that the therapeutic agents are administered at a different time, either before or after, the administration of the therapeutics described herein. The separation in time between the administration of these compounds may be a matter of minutes or it may be longer.

Thus, in some instances, the invention also involves administering another cancer treatment (e.g., radiation therapy, chemotherapy or surgery) to a subject. Examples of conventional cancer therapies include treatment of the cancer with agents such as All-trans retinoic acid, Actinomycin D, Adriamycin, anastrozole, Azacitidine, Azathioprine, Alkeran, Ara-C, Arsenic Trioxide (Trisenox), BiCNU Bleomycin, Busulfan, CCNU, Carboplatin, Capecitabine, Cisplatin, Chlorambucil, Cyclophosphamide, Cytarabine, Cytoxan, DTIC, Daunorubicin, Docetaxel, Doxifluridine, Doxorubicin, 5-flurouracil, Epirubicin, Epothilone, Etoposide, exemestane, Erlotinib, Fludarabine, Fluorouracil, Gemcitabine, Hydroxyurea, Herceptin, Hydrea, Ifosfamide, Irinotecan, Idarubicin, Imatinib, letrozole, Lapatinib, Leustatin, 6-MP, Mithramycin, Mitomycin, Mitoxantrone, Mechlorethamine, megestrol, Mercaptopurine, Methotrexate, Mitoxantrone, Navelbine, Nitrogen Mustard, Oxaliplatin, Paclitaxel, pamidronate disodium, Pemetrexed, Rituxan, 6-TG, Taxol, Topotecan, tamoxifen, taxotere, Teniposide, Tioguanine, toremifene, trimetrexate, trastuzumab, Valrubicin, Vinblastine, Vincristine, Vindesine, Vinorelbine, Velban, VP-16, and Xeloda.

Cancer therapies and their dosages, routes of administration and recommended usage are known in the art and have been described in such literature as the *Physician's Desk Reference* (56th ed., 2002). In some embodiments, the therapeutic compounds of the invention are formulated into a pharmaceutical composition that further comprises one or more additional anticancer agents.

The active agents of the invention are administered to the subject in an effective amount for treating the subject. An "effective amount", for instance, is an amount necessary or sufficient to realize a desired biologic effect. For instance an effective amount is that amount sufficient to prevent or inhibit cancer cell growth or proliferation or alternatively an amount sufficient to induce apoptosis of a cancer cell or induce tumor regression.

The effective amount of a compound of the invention in the treatment of a subject may vary depending upon the specific compound used, the mode of delivery of the compound, and whether it is used alone or in combination. The effective amount for any particular application can also vary depending on such factors as the type and/or degree of cancer in a subject, the particular compound being administered for treatment, the size of the subject, or the severity of the disorder. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity in and of itself and yet is entirely effective to treat the particular subject.

Toxicity and efficacy of the protocols of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays, animal studies and human studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

Multiple doses of the molecules of the invention are also contemplated. In some instances, when the molecules of the invention are administered with another therapeutic, for instance, a chemotherapeutic agent a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The compounds may be sterile or non-sterile.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In general, a pharmaceutical composition comprises the compound of the invention and a pharmaceutically-acceptable carrier. Pharmaceutically-acceptable carriers for nucleic acids, small molecules, peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In one embodiment, a kit comprises a reagent for detecting CD80. The kit may further comprise assay diluents, standards, controls and/or detectable labels. The assay diluents, standards and/or controls may be optimized for a particular sample matrix. Reagents include, for instance, antibodies, nucleic acids, labeled secondary agents, or in the alternative, if the primary reagent is labeled, enzymatic or agent binding reagents which are capable of reacting with the labeled reagent. One skilled in the art will readily recognize that reagents of the present invention can be readily incorporated into one of the established kit formats which are well known in the art.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment or characterization of a cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Methods

Cell Line Derivation:

Tumors were isolated from $Kras^{LA2/+}$; $Trp53^{LSL/LSL}$; $Rosa26^{CreERT2}$ animals, dissociated with collagenase and trypsin for one hour at 37° C., and then grown in DME plus 10% fetal bovine serum. Human cell lines were obtained from American Type Culture Collection and grown per manufacturer recommendations.

Mice:

NCRNuM mice were obtained from Taconic Inc. Tumor cells were injected into the lateral tail vein ($4 \times 10^5$ cells in 200 µL PBS). Tamoxifen (Sigma) was dissolved in corn oil (Sigma) and administered i.p. twice weekly at a 200 µg/g total body weight. Tumor burden was measured on an IVIS Spectrum Instrument (Caliper Life Sciences) ten minutes after i.p. injection of a 100 µL solution of 15 mg/mL Luciferin.

Gene Expression Analyses:

RNA was isolated from cultured cells with Trizol reagent following manufacturer protocol. Complementary DNA was generated from 1 µg total RNA using High Capacity RT-PCR Kit (Roche, quantitative PCR (Q-RT-PCR)) following manufacturer protocol. Total cDNA was diluted 20 fold in H2O and 10 µL was used in a SYBR green quantitative PCR reaction. Specifically, specific primers were diluted from 100 µM stocks to a final concentration of 0.25 µM into JumpStart Ready Taq SYBR green (Sigma) and 10 µL was mixed with 10 µL diluted cDNA and cycled 40 times with the following cycling parameters on a Step One Plus (Applied Biosystems) real-time thermocycler:

Cycle Parameters:

| | |
|---|---|
| 94° C. | 2 minutes |
| 94° C. | 15 seconds |
| 60° C. | 1 minute |

Specific Primer Sequences were:

```
                                          (SEQ ID NO 1)
CD80 Forward: tcgtctttcacaagtgtcttcag (SEQ ID NO 2)
CD80 Reverse: ttgccagtagattcggtcttc
```

Flow Cytometry:

Cells were harvested from plasticware using 2 mM EDTA solution. Approximately 1 X106 cells were resuspended in % FBS in PBS and incubated with APC conjugated CD80 Ab at a 1:100 dilution (Hamster IgG2 Clone:16-10A1 from BD Biosciences). Cells were scanner on a FASCaliber flow cytometer (BD Biosciences).

Statistics:

P values were determined by Student t tests.

Results p53 restoration causes tumor regression in lung cancer in mice. This is depicted schematically in FIG. 1. It is shown that inducible p53 function in mouse lung adenocarcinoma cell line transplants.

Figure 2:
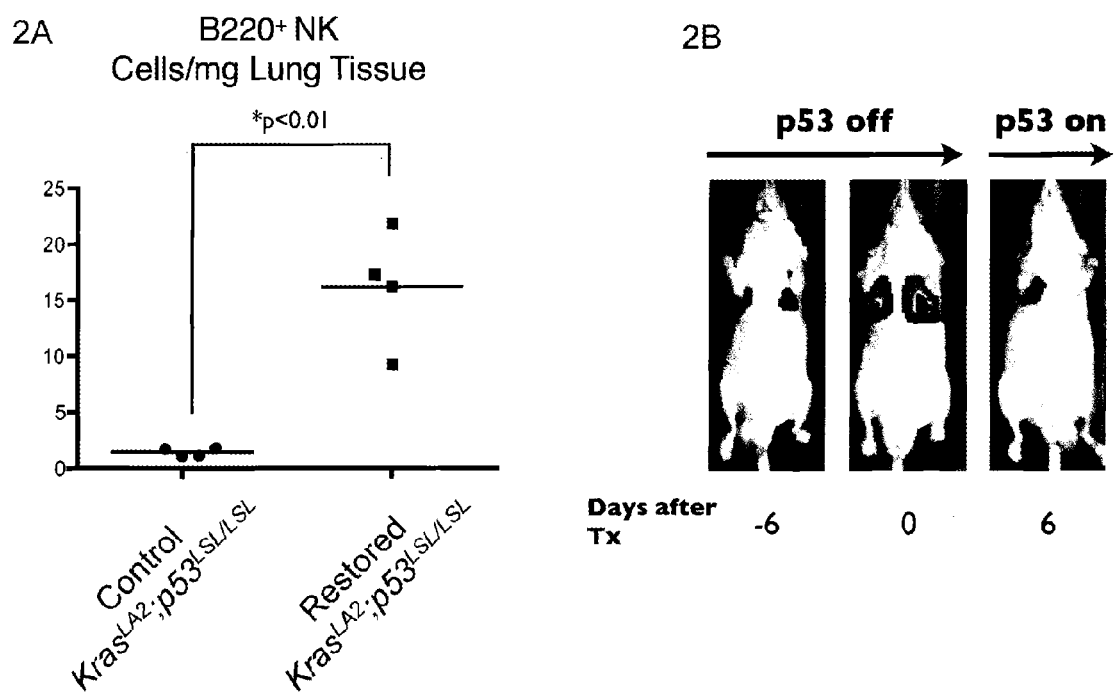
FIG. 2 shows tumor regression and NK cell activation in transplanted tumors after p53 restoration.
Figure 3:
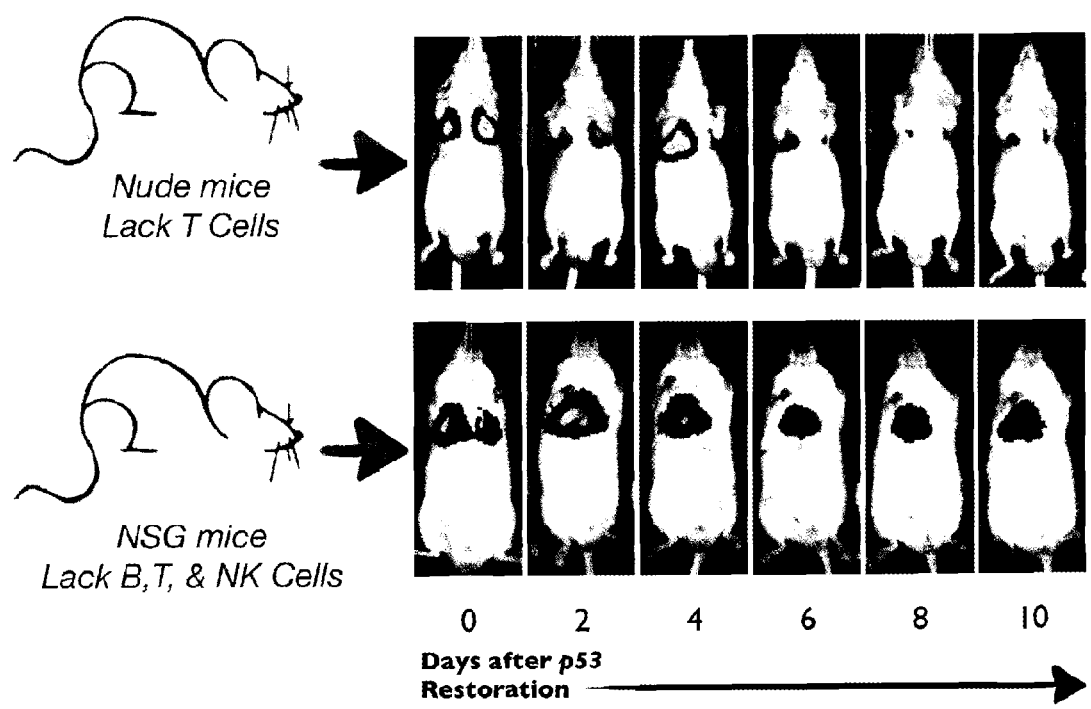
FIG. 3 demonstrates that NK cell lineages are required for tumor regression after p53 restoration.
Figure 4:
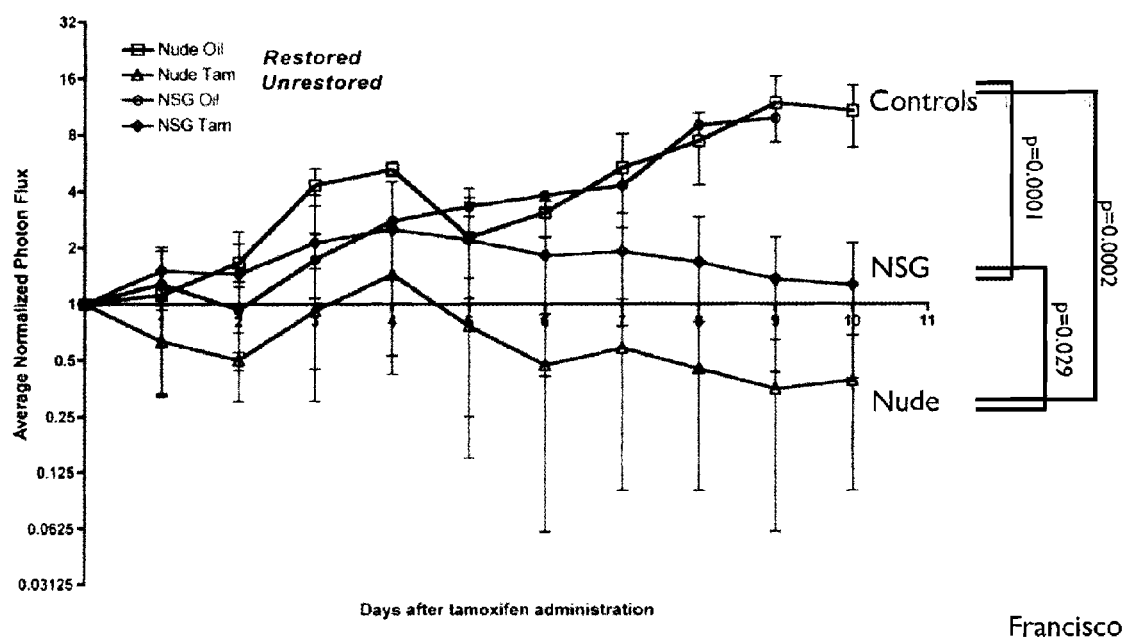
FIG. 4 is a graph demonstrating that tumor regression is more robust in NCR Nu/Nu than NSG recipients.

Tumors were found to regress and NK cells were activated in transplanted tumors after p53 restoration. The results are shown in FIG. 2. In particular FIG. 2A is a graph depicting the amount of B220+NK cells/mg lung tissue for either control or restored KrasLA2; p53LSL/LSL. FIG. 2B is a photograph of mice treated as in FIG. 2A, before, at the time and following treatment. The requirement of NK cell lineages in tumor regression after p53 restoration is shown in FIG. 3-4. As shown in FIG. 4 it was demonstrated that tumor regression is more robust in NCR Nu/Nu than NSG recipients.

Figure 5:
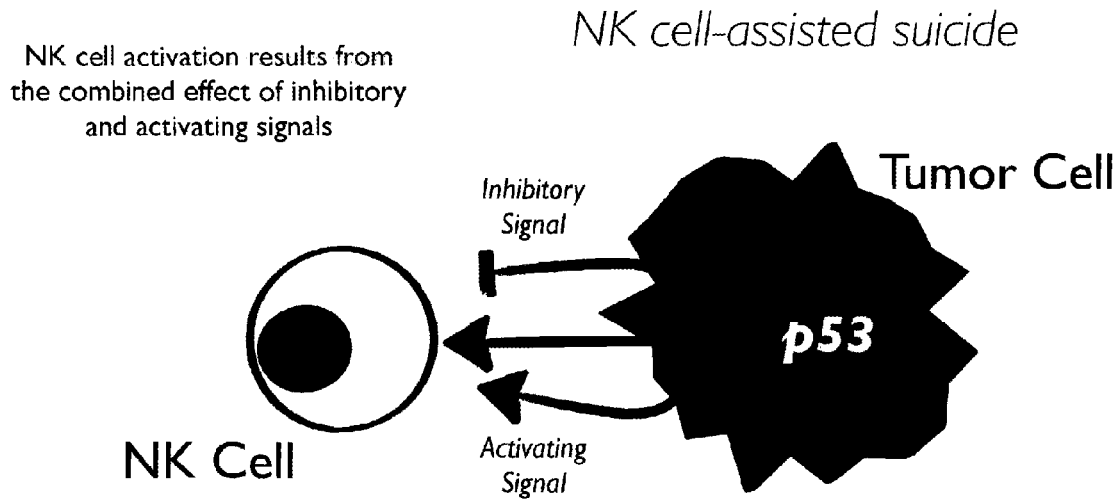
FIG. 5 is a schematic showing the molecular determinants of the p53tumor immune surveillance network—NK cell activation results from the combined effect of inhibitory and activating signals.

The molecular determinants of the p53 tumor immune surveillance network including NK cell activation resulting from the combined effect of inhibitory and activating signals is shown schematically in FIG. 5.

Figure 6:
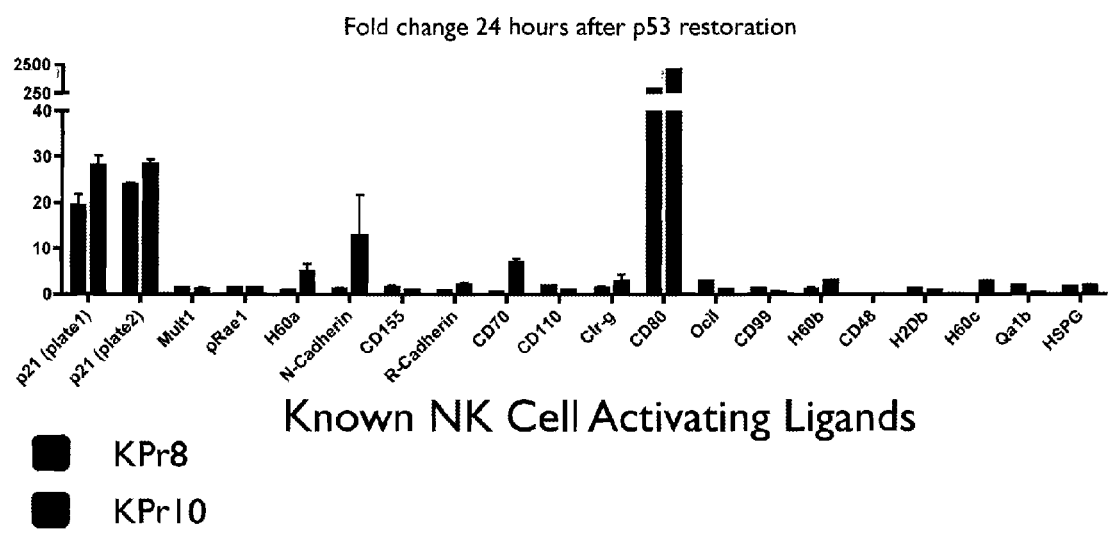
FIG. 6 is a graph demonstrating that CD880 mRNA is selectively induced upon p53 restoration. Many other known NK cell activating ligands are not induced.
Figure 7:
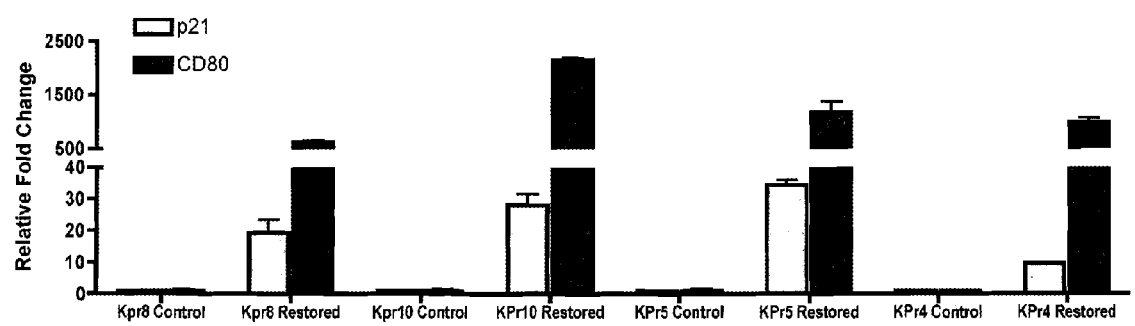
FIG. 7 is a graph demonstrating that CD80 is a putative NK cell activating ligand.
Figures 8E, 8F:
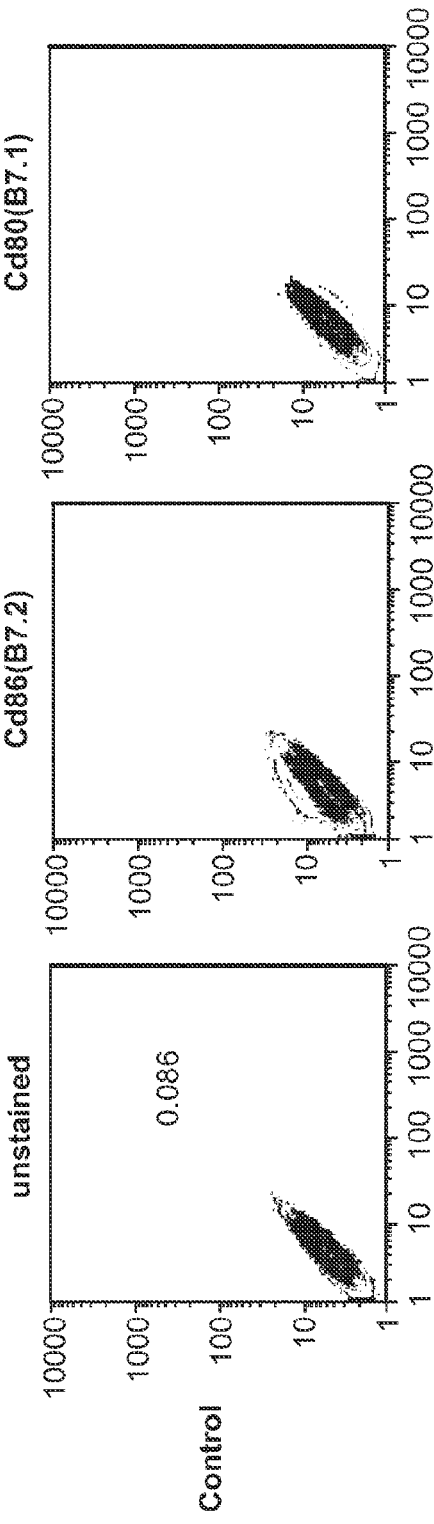
FIG. 8 is data from a flow cytometric analysis of CD80 (8C and 8F) versus CD86 (8B and 8E) cell surface expression in response to p53 restoration in the form of contour plots. The top panel (8A, 8B, and 8C) represents control cells wherein p53 is not restored. The bottom panel (8D, 8E, and 8F) represents cells 48 hours after p53 restoration.
Figure 9A:
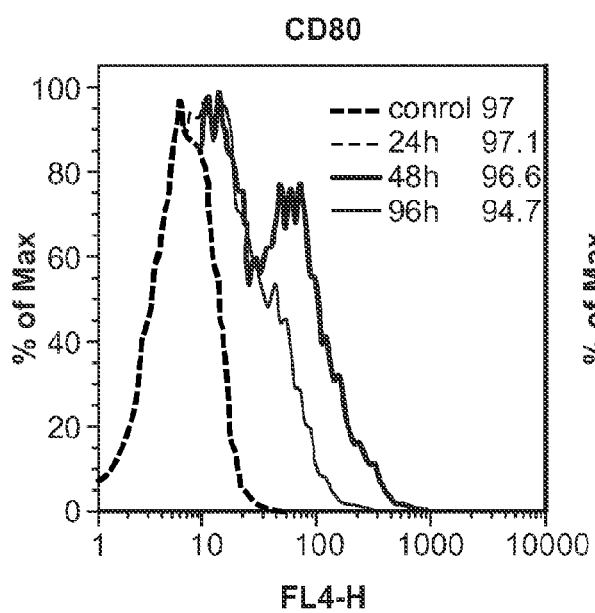
FIG. 9 is a set of flow cytometry histograms demonstrating that CD80 cell surface expression increases with time following p53 restoration in cells in culture (9A). A control, shows that MHC expression does not change with time, as expected (9B).
Figure 9B:
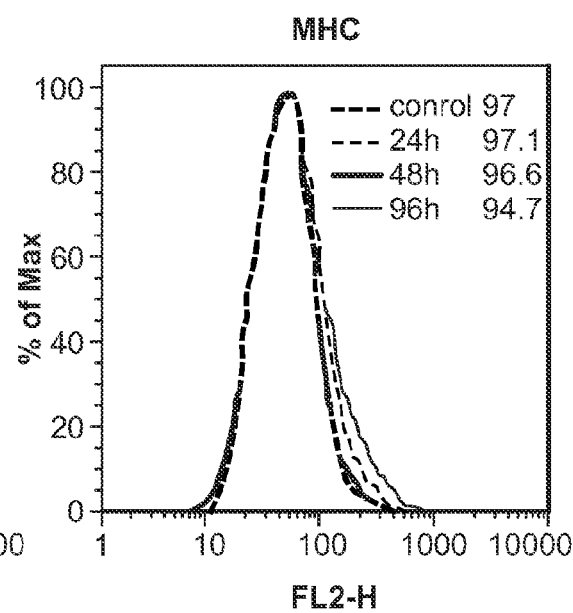
Figure 10:
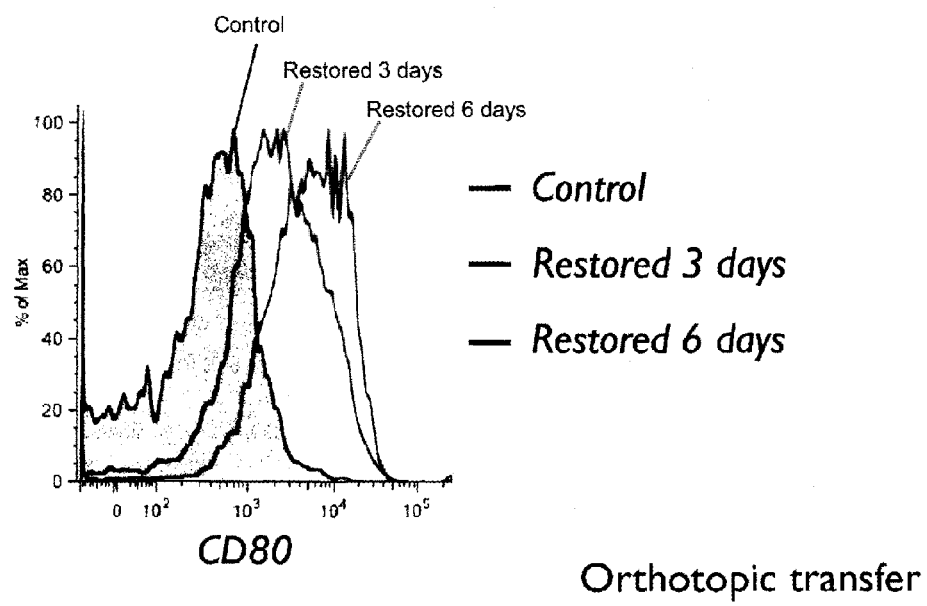
FIG. 10 is a flow cytometry histogram demonstrating that CD80 cell surface expression increases with time following p53 restoration for 3 days or 6 days in cells that have undergone orthopic transfer.
Figure 11A:
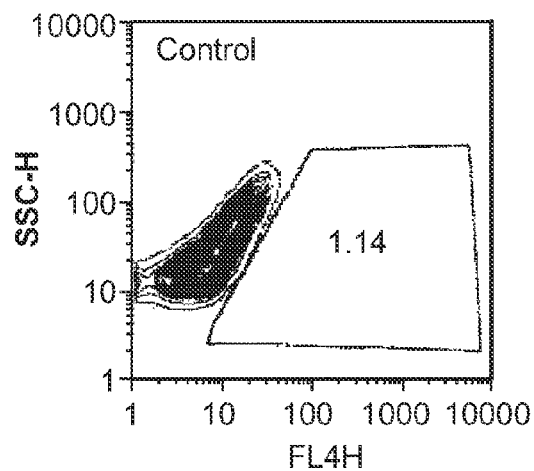
FIG. 11 is a set of flow cytometry histograms demonstrating that CD80 cell surface expression is not tamoxifen dependent. Cells were either untreated (11A), treated with tamoxifen (11B), treated with AdFlpO (11C), or treated with AdCre (11D).
Figure 11B:
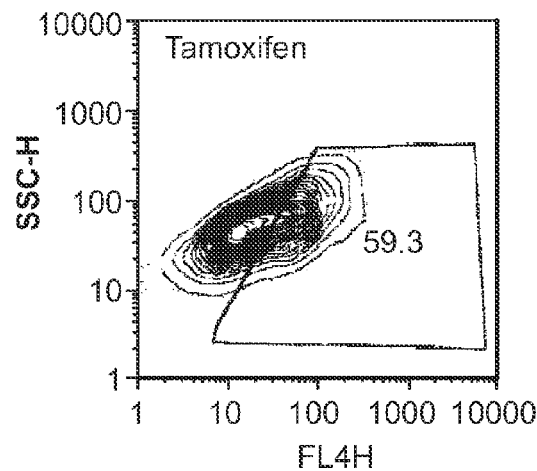
Figure 11C:
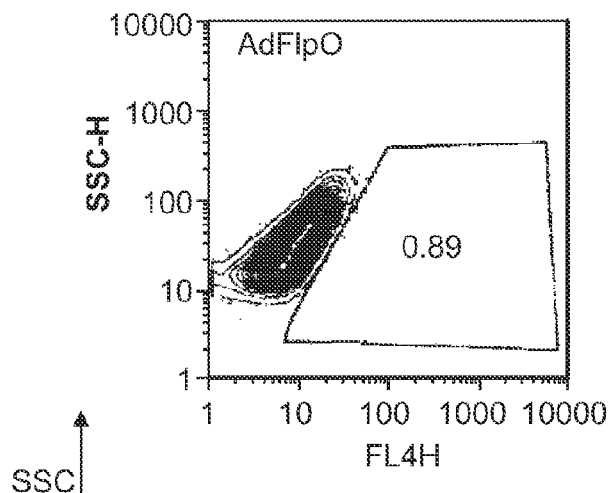
Figure 11D:
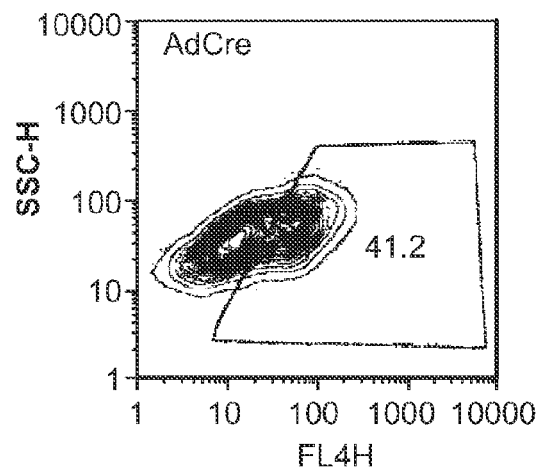

The methods of the invention led to the discovery that CD80 is selectively induced upon p53 restoration and that CD80 functions through NK cells. The data is shown in FIGS. 6-7. The specificity of the cell surface CD80 induction was demonstrated using flow cytometry. The results are shown in FIGS. 8-11.

Figure 12:
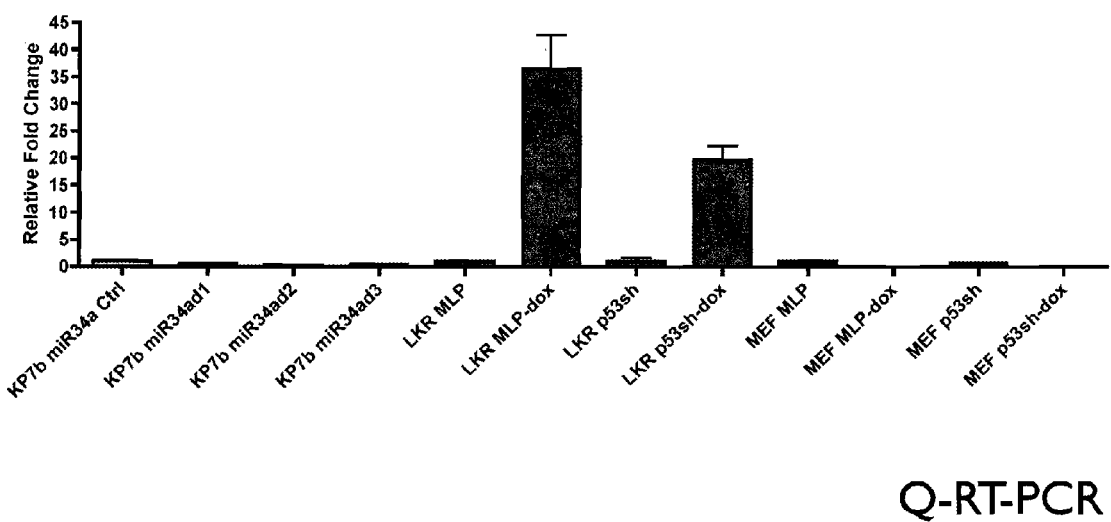
FIG. 12 is a graph demonstrating that CD80 is induced by p53 restoration in lung cancer cells (LKR) but not in primary MEFs or by p53-independent cytostatic effects of mir34a in cancer cells. The data was generated using Q-RT-PCR and is expressed as a relative fold change in CD80.
Figure 13:
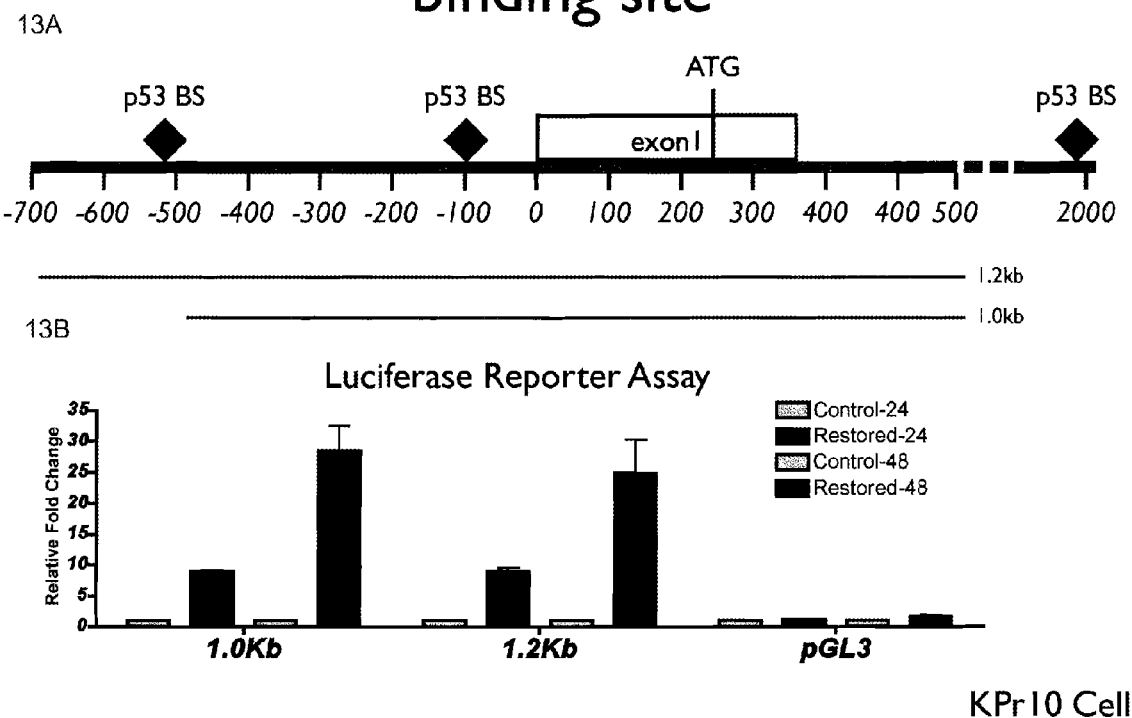
FIG. 13A shows a mouse CD80 gene with consensus p53 binding site.
FIG. 13B is a graph depicting the results of a luciferase reporter assay on control or p53 restored KPr10 cells, 24 or 48 hours after treatment to demonstrate the presence of p53 binding site.

FIG. 12 is a graph demonstrating that CD80 is induced by p53 restoration in lung cancer cells (LKR) but not in primary MEFs or by the p53-independent cytostatic effects of mir34a in cancer cells. The data was generated using Q-RT-PCR and is expressed as a relative fold change in CD80. A mouse CD80 gene with consensus p53 binding site is shown in FIG. 13.

Figure 14:
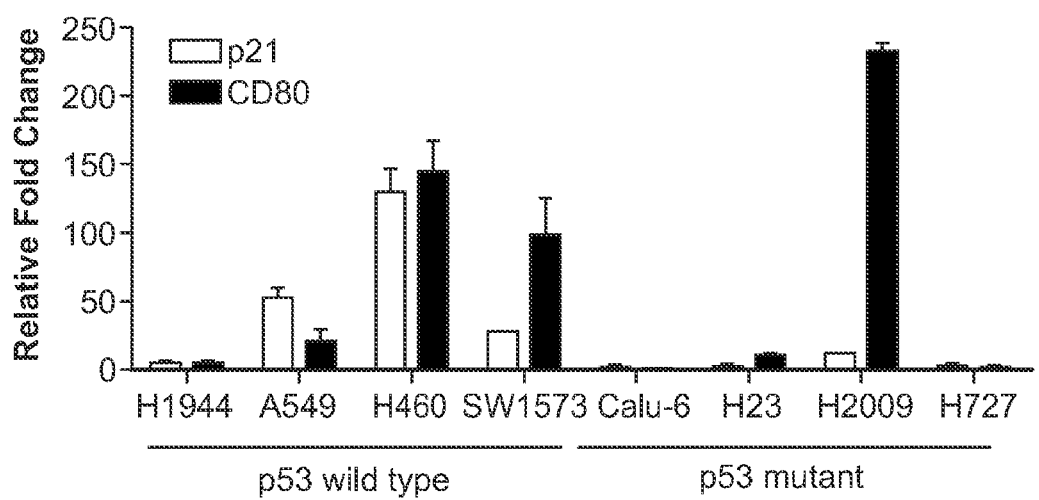
FIG. 14 is a graph depicting the amount of doxorubicin induced p21 and CD80, as measured by Q-RT-PCR, in a set of p53 wild type or p53 mutant cells. It was demonstrated that induction of human CD80 mirrors p21 induction.

It was also discovered that doxorubicin induced p21 and CD80, as measured by Q-RT-PCR, in a set of p53 wild type or p53 mutant cells. It was demonstrated that induction of human CD80 mirrors p21 induction. The results are shown in FIG. 14.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method, comprising determining the status of p53 in a cancer cell of a subject and administering to the subject an anti-CD80 antibody when the cancer cell has normal p53 or is induced to have p53 activity, such that the cancer cell expresses CD80, wherein the anti-CD80 antibody is conjugated to a toxic compound.

2. The method of claim 1, wherein the method further comprises the step of determining whether subject has a CD80 positive cancer.

3. The method of claim 1, wherein the p53 is a p53 mutant that is capable of supporting p53 activity when treated with a p53 inducing agent.

4. The method of claim 3, wherein the p53 inducing agent is a p53 expression inducing agent.

5. The method of claim 3, wherein the p53 inducing agent is a p53 activity inducing agent.

6. The method of claim 1, wherein the p53 is a normal p53.

7. The method of claim 1, further comprising administering to the subject a chemotherapeutic agent.

8. The method of claim 1, wherein the cancer cell is a lung cancer cell.

9. A method of treating a subject having cancer, comprising administering to a subject having cancer an anti-CD80 antibody and a p53 inducing agent in an effective amount to treat the subject having cancer, wherein the cancer expresses CD80, and wherein the anti-CD80 antibody is conjugated to a toxic compound.

* * * * *